(12) United States Patent
Kaneko et al.

(10) Patent No.: US 6,814,797 B2
(45) Date of Patent: Nov. 9, 2004

(54) GEL COMPOSITION AND NAIL ENAMEL

(75) Inventors: Katsuyuki Kaneko, Yokohama (JP);
Hirotaka Takada, Yokohama (JP);
Tsuneo Suhara, Yokohama (JP);
Yoshikazu Soyama, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 302 days.

(21) Appl. No.: 10/070,757

(22) PCT Filed: Jul. 13, 2001

(86) PCT No.: PCT/JP01/06078

§ 371 (c)(1),
(2), (4) Date: Mar. 12, 2002

(87) PCT Pub. No.: WO02/05756

PCT Pub. Date: Jan. 24, 2002

(65) Prior Publication Data

US 2003/0124072 A1 Jul. 3, 2003

(30) Foreign Application Priority Data

Jul. 13, 2000 (JP) ........................ 2000-212989

(51) Int. Cl.[7] .................................. C08K 5/00
(52) U.S. Cl. .................. 106/499; 106/487; 106/499; 424/61
(58) Field of Search ................. 106/487, 499; 424/61

(56) References Cited

U.S. PATENT DOCUMENTS 3,422,185 A * 1/1969 Kuritzkes .................. 424/61
5,202,114 A * 4/1993 Ogusu et al. ............... 424/61

FOREIGN PATENT DOCUMENTS

| JP | 57-027300 | 8/1983 |
| JP | 07-223926 A | 8/1995 |
| JP | 09-002816 A | 1/1997 |
| JP | 09-175817 A | 7/1997 |
| JP | 11-228351 A | 8/1999 |
| WO | WO 89/12500 A1 | 12/1989 |
| WO | WO 98/54271 A1 | 12/1998 |

* cited by examiner

Primary Examiner—C. Melissa Koslow
Assistant Examiner—Shalie Manlove
(74) Attorney, Agent, or Firm—Fei-Fei Chao; Venable LLP

(57) ABSTRACT

The present invention provides a gel composition capable of maintaining a high viscosity controlling ability over a wide polarity range from a low to a high polarity and also capable of exhibiting an excellent viscosity stability over a prolonged period as well as such nail enamel. The composition comprises cation-modified clay mineral, wherein cations of said cation-modified clay mineral comprise quaternary ammonium cation represented by Formula (I):

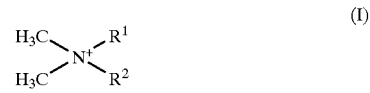

wherein $R^1$ is a $C_{1-9}$ alkyl group, a phenyl group or a $C_{7-9}$ aralkyl group and $R^2$ is a $C_{10-36}$ alkyl group, and Formula (II):

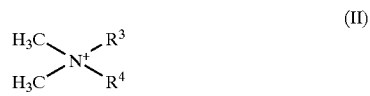

wherein $R^3$ and $R^4$ are independent from each other and each represents a $C_{10-36}$ alkyl group. Preferably, said cation-modified clay mineral comprises cation-modified clay minerals A and B whose cations are Cations (I) and (II) respectively in a weight ratio of A:B from 55:45 to 99.9:0.1.

9 Claims, No Drawings

GEL COMPOSITION AND NAIL ENAMEL

This application claims the priority of Japanese Patent Application No. 2000-212989 filed on Jul. 13th, 2000, which is incorporated herein by reference.

FIELD OF THE INVENTION

The present invention relates to a gel composition and a nail enamel; and, in particular, to an improvement in viscosity controlling ability and stability thereof.

BACKGROUND OF THE INVENTION

Since a cation-modified clay mineral obtained by replacing an exchangeable cation being between crystal layers in a clay mineral with an organic cation such as a quaternary ammonium cation forms a satisfactory oily gel having a thixotropic property, it is incorporated into a product such as a paint or a nail enamel as a pigment sedimentation-preventing agent. A gelation mechanism which is proposed currently is that an organic solvent introduces into a cation site between crystal layers of a cation-modified clay mineral to enlarge a space between the layers, whereby effecting a gelation.

However, a change in the polarity of the solvent leads to a problematically substantial change in the viscosity since the gelation ability (viscosity controlling ability) may vary greatly depending on the suitability between the type of the cation and the polarity of the solvent. For example, a product containing a substantial amount of an organic solvent such as a nail enamel or a paint tends to change in the polarity due to the evaporation of the solvent, which may reduce the viscosity or the sedimentation-preventing effect.

SUMMARY OF THE INVENTION

The present invention is performed in view of the problems associated with the art described above, and its objective is to provide a gel composition capable of maintaining a high viscosity controlling ability over a wide polarity range from a low polarity to a high polarity and also capable of exhibiting an excellent viscosity stability over a prolonged period as well as such nail enamel.

In order to accomplish the objective, the inventors have carried out delligent studies and finally found that the problems described above can be solved by using two certain quaternary ammonium cations as substitute cations for cation-modified clay mineral at a certain weight ratio, whereby accomplishing the present invention.

Namely, a gel composition of the present invention comprises cation-modified clay mineral, wherein cations of said cation-modified clay mineral, wherein cations of said cation-modified clay mineral comprise quaternary ammonium cations represented by Formula (I):

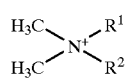
(I)

wherein $R^1$ is a $C_{1-9}$ alkyl group, a phenyl group or a $C_{7-9}$ aralkyl group and $R^2$ is a $C_{10-36}$ alkyl group, and Formula (II):

(II)

wherein $R^3$ and $R^4$ are independent from each other and each representes a $C_{10-36}$ alkyl group.

In the gel composition of the present invention, said cation-modified clay mineral preferably comprises a cation-modified clay mineral A whose cation is the quaternary ammonium cation represented by Formula (I) and a cation-modified clay mineral B whose cation is the quaternary ammonium cation represented by Formula (II) in a weight ratio of A:B from 55:45 to 99.9:0.1, more preferably from 60:40 to 80:20.

$R^1$ is preferably benzyl group.

$R^1$ is preferably methyl group.

$R^2$ is preferably a $C_{16-18}$ alkyl group.

Eeach of $R^3$ and $R^4$ is preferably a $C_{16-18}$ alkyl group.

A host clay mineral of said cation-modified clay mineral is preferably montmorillonite or hectorite, more preferably montmorillonite.

A nail enamel of the present invention comprises any of gel compositions described above.

BEST MODES FOR CARRYING OUT THE INVENTION

In Formula (I), the $C_{1-9}$ alkyl group of $R^1$ may be a straight or branched chain. Examples thereof include methyl, ethyl, propyl, isopropyl, butyl, tert-butyl. hexyl, octyl, and nonyl group. Preferably, it is methyl group.

The $C_{7-9}$ aralkyl group of $R^1$ may be benzyl group, phenethyl and so on. Preferably, it is benzyl group.

The $C_{10-36}$ alkyl group of $R^2$ may be a straight or branched chain. Examples thereof include decyl, undecyl, 6-methyldecyl, dodecyl, tridecyl, tetradecyl, hexadecyl, octadecyl, 2-ethylhexadecyl, icosyl, henicosyl, docosyl, tetoracosyl, 22-methyltetracosyl, hexacosyl, octacosyl, and 2-dodecyloctadecyl group. Preferably, it is a $C_{16-18}$ alkyl group, particularly preferably hexadecyl or octadecyl group.

Preferable examples of Cation(I) include hexadecyldimethylbenzyl-ammonium, octadecyldimethylbenzylammonium, hexadecyltrimethylammonium and octadecyltrimethylammonium.

In Formula (II), the $C_{10-36}$ alkyl group of $R^3$ or $R^4$ is as defined in $R^2$ mentioned above. Preferably, it is a $C_{16-18}$ alkyl group, particular preferably hexadecyl or octadecyl group.

Preferable examples of Cation(II) include dihexadecyldimethylammonium and dioctadecyldimethylammonium.

The clay mineral (as a host) which is exchanged with Cation (I) or Cation (II) may be a water-swollen clay mineral which is one of hydrated colloidal aluminum silicates having three-layered structures, such as natural or synthetic clay mineral including bentonite, montmorillonite, hectorite, saponite and the like. Preferably, it is montmorillonite or hectorite, particularly preferably montmorillonite.

The cation-modified clay mineral employed in the present invention can be prepared by a known method. For example, it can be obtained by: dissolving a salt of the cation described above such as a quaternary ammonium salt whose counter ion is a halogen ion (e.g., chloride ion), nitrite ion, hydroxyl ion, acetate ion, methyl sulfate ion, or the like in an ion-exchange water; adding and dispersing the host clay mineral; and then collecting by filteration and drying the resulting precipitates. More conveniently, a commercial product may also be used.

An especially preferred example of the cation-modified clay mineral A whose cation is Cation (I) is one wherein $R^1$ is benzyl, $R^2$ is octadecyl and the clay mineral is montmorillonite. Examples of commercial products thereof include TIXOGEL-MPZ and TIXOGEL-MP250 (manufactured by Sud-Chemie Rheologicals).

An especially preferred example of the cation-modified clay mineral B whose cation is Cation (II) is one wherein each of $R^3$ and $R^4$ is octadecyl and the clay mineral is montmorillonite. Examples of commercial products thereof include TIXOGEL-MP and TIXOGEL-MP100 (manufactured by Sud-Chemie Rheologicals).

In the present invention, two or more cation-modified clay minerals A may be employed. Also, a cation-modified clay mineral A resulting from the exchange with two or more Cations (I) can be used. Similarly, two or more cation-modified clay minerals B may be employed. Also, a cation-modified clay mineral B resulting from the exchange with two or more Cations (II) can be used.

In the present invention, the weight ratio between the cation-modified clay minerals A and B as a whole may be 55:45 to 99.9:0.1, preferably 60:40 to 80:20. It is also possible in the present invention to employ a cation-modified clay mineral resulting from the exchange with both of Cation (I) and Cation (II). An example of commercial products is TIXOGEL-UN (manufactured by Sud-Chemie Rheologicals). In such case, this cation-modified clay mineral may be regarded as a mixture of a cation-modified clay mineral A whose cation is only Cation (I) and a cation-modified clay mineral B whose cation is only Cation (II), and the ratio between cation-modified clay minerals A and B caluculated from the level of the exchange with Cation (I) and Cation (II) should be within the range specified above.

While the amount of the cation-modified clay mineral in a gel composition may vary depending on the intended product, it is usually 1 to 20% by weight. In a nail enamel, the amount is usually 0.05 to 10% by weight, preferably 1 to 5% by weight. An excessive amount may lead to an adverse effect on the gloss or the long-lasting performance of the nail enamel coating.

A gel composition of the present invention may contain other components as long as the advantageous property of the present invention is not affected adversely.

As for a surfactant, any of nonionic surfactants, anionic surfactants, cationic surfactants and amphoteric surfactants may be incorporated. Particularly, when a polyoxyethylene/polyoxypropylene (POE/POP) chain-containing cationic surfactant described in JP-A-2-56239 is used, it is can be easy to disperse the cation-modified clay mineral uniformly. It is also preferable to incorporate an anionic surfactant besed on a phosphate ester, a carboxylic acid, a sulfonic acid, a sulfate ester or the like.

As for a film-forming agent, Nitrocelluolse ½ second, Nitrocellulose ¼ second, Nitrocellulose ⅛ second, Nitrocellulose 1/16 second or the like can be used.

A resin may for example be an alkyd-based resin, a polyester-based resin, a sucrose-based resin, a sulfomamide-based resin, a rosin-based resin, a phenolic resin, an amino-based resin, an epoxy-based resin, an acryl silicone resin or the like.

A plasticizer may for example be dibutyl phthalate, dioctyl phthalate, tributyl citrate, acetyltributyl citrate, acetyltriethyl citrate, camphor or the like.

A solvent employed is a volatile solvent in which nitrocellulose is soluble, including a ketone such as acetone, methyl ethyl ketone, methyl isobutyl ketone or diisobutyl ketone; an acetate such as ethyl acetate, isopropyl acetate, n-butyl acetate, isobutyl acetate or amyl acetate; a cellosolve such as methyl cellosolve, butyl cellosolve, phenyl cellosolve, benzyl cellosolve or cellosolve acetate; and a carbitol such as methyl carbitol or butyl carbitol.

In addition, a solubilizing adjuvant such as ethanol, isopropanol or butanol can be employed.

Otherwise, toluene, xylene, benzol, solvent naphtha or the like may be employed as a diluent.

Examples of a powder include: an inorganic powder such as talc, kaolin, sericite, muscovite, synthetic mica, phlogopite, carmine mica, biotite, lepidolite, vermiculite, magnesium carboante, calcium carbonate, kiesel guhr, magnesium silicate, calsium silicate, aluminum silicate, barium silicate, barium sulfate, strontium silicate, metal tungstate, silica, hydroxyapatite, zeolite, boron nitride or ceramic powder; an organic powder such as nylon powder, polyethylene powder, benzoguanamine powder, ethylene tetrafluoride powder, styrene divinylbenzene copolymer powder, distyrene benzene pinhole polymer powder or microcrystalline cellulose; an inorganic white pigment such as titanium oxide or zinc oxide; an inorganic red pigment such as iron oxide (iron oxide red) or iron titanate; an inorganic brown pigment such as γ-iron oxide; an inorganic yellow pigment such as iron oxide yellow or loess; an inorganic black pigment such as iron oxide black or carbon black; an inorganic purple pigment such as mango-violet or cobalt violet; an inorganic green pigment such as chromium oxide, chromium hydroxide or cobalt titanate; an inorganic blue pigment such as ultramarine or cobalt blue; a pearl pigment such as titanium oxide-coated bismuth oxychloride, bismuth oxychloride, titanium oxide-coated talc, pearlessence or colored titanium oxide-coated mica; a clay mineral such as Benton, a metal powder pigment such as aluminum powder or copper powder; an organic pigment such as Red #210, Red #202, Red #204, Red #205, Red #220, Red #226, Red #228, Red #405, Orange #203, Orange #204, Yellow #205, Yellow #401 or blue #404; zicorium-,barium- or aluminum-derived organic lake pigment such as Red #3, Red #104, Red #106, Red #227, Red #230, Red #401, Red #505, Orange #205, Yellow #4, Yellow #5, Yellow #202, Yellow #203, Green #3 or Blue #1; a natural coloring matter such as chlorophyll or β-carotene as well as magnesium oxide, magnesium hydroxide, calcium oxide, calcium hydroxide, aluminum oxide, aluminum hydroxide, silica, iron hydroxide, titanium dioxide, low-order titanium oxide, zirconium oxide, chromium oxide, chromium hydroxide, manganese oxide, cobalt oxide, nickel oxide, iron titanate, cobalt titanate, cobalt aluminate and the like.

Otherwise, a UV absorber, a humectant, a medicament, a fragrance, a water-soluble component or additional solvents can also be incorporated.

The present invention is further described in the following typical examples. Unless otherwise specified, an amount is a % by weight. An amount of nitrocellulose is as a 30% solution in isopropyl alcohol (IPA). The cation-modified clay minerals employed here are shown in Table 1.

TABLE 1

| Cation-modified clay mineral No. | Chemical name |
| --- | --- |
| A1 | octadecyldimethylbenzylammonium chloride-modified montmorillonite (MPZ) |
| A2 | hexadecyldimethylbenzylammonium chloride-modified montmorillonite |
| A3 | trimethyloctadecylammonium chloride-modified montmorillonite |
| A4 | octadecyldimethylbenzylammonium chloride-modified hectorite (Benton 27) |
| B1 | dioctadecyldimethylammonium chloride-modified montmorillonite (MP100) |
| B2 | dihexadecyldimethylammonium chloride-modified montmorillonite |
| B3 | dioctadecyldimethylammonium chloride-modified hectorite (Benton 38) |

EXPERIMENT EXAMPLE 1

Viscosity Controlling Ability

| (Gel composition formulation) | |
| --- | --- |
| Nitrocellulose | 20% by weight |
| Toluenesulfonamide | 15 |
| Acetyltributyl citrate | 5 |
| Camphor | 2 |
| Ethyl acetate + n-butyl acetate | 54.4 |
| n-Butanol | 1 |
| POE(1)POP(25)diethylmethylammonium chloride | 0.5 |
| Di-POE(2)myristyl ether phosphoric acid | 0.1 |
| Cation-modified clay minerals (A1 + B1) | 2 |

Experimental Method

Gel compositions were prepared with varying the ratio of ethyl acetate/n-butyl acetate and the ratio of Cation-modified clay minerals A1/B1. The preparation was accomplished by mixing the components and stirring with HOMODISPER to produce a gel composition. The viscosity of each composition was evaluated based on the criteria shown below.

⊚: Good thickening ability
○: Slightly good thickening ability
Δ: Slightly poor thickening ability
×: Poor thickening ability

TABLE 2

| | Ethyl acetate/n-butyl acetate ratio | | | | |
| --- | --- | --- | --- | --- | --- |
| A1/B1 ratio | 0/100 | 25/75 | 50/50 | 75/25 | 100/0 |
| 0/100 | Δ | Δ | X | X | X |
| 25/75 | Δ | Δ | Δ | X | X |
| 50/50 | Δ | Δ | Δ | Δ | Δ |
| 55/45 | ○ | ○ | ○ | ○ | ○ |
| 60/40 | ⊚ | ⊚ | ⊚ | ⊚ | ⊚ |
| 70/30 | ⊚ | ⊚ | ⊚ | ⊚ | ⊚ |
| 80/20 | ⊚ | ⊚ | ⊚ | ⊚ | ⊚ |
| 99.9/0.1 | ○ | ○ | ○ | ○ | ○ |
| 100/0 | X | Δ | Δ | Δ | ○ |

As shown in Table 2, any of Cation-modified clay minerals A1 and B1, when employed alone, exhibited a thickening ability which was not satisfactory at any solvent ratio and which varied depending on the solvent ratio.

On the contrary, a use of a combination of Cation-modified clay minerals A1 and B1 resulted in an increase in the thickening ability. Especially at an A1/B1 ratio from 55:45 to 99.9:0.1, almost no solvent ratio-dependent change in the viscosity was observed In addition, an A1/B1 ratio from 60:40 to 80:20 resulted in an extremely high thickening ability and enabled an inhibition of the solvent ratio-dependent change in the viscosity.

EXPERIMENT EXAMPLE 2

Stability Over a Prolonged Period

T gel composition of Experiment Example 1 was filled in a container and stored at 50° C. After 1 month, it was observed visually for any sedimentation or separation and evaluated based on the criteria shown below.

⊚: No sedimentation or separation was observed.
○: Almost no sedimentation or separation was observed.
Δ: Sedimentation or separation was observed.
×: Remarkable sedimentation or separation was observed.

TABLE 3

| | Ethyl acetate/n-butyl acetate ratio | | | | |
| --- | --- | --- | --- | --- | --- |
| A1/B1 ratio | 0/100 | 25/75 | 50/50 | 75/25 | 100/0 |
| 0/100 | Δ | Δ | X | X | X |
| 25/75 | Δ | Δ | Δ | X | X |
| 50/50 | Δ | Δ | Δ | Δ | Δ |
| 55/45 | ○ | ○ | ○ | ○ | ○ |
| 60/40 | ⊚ | ⊚ | ⊚ | ⊚ | ⊚ |
| 70/30 | ⊚ | ⊚ | ⊚ | ⊚ | ⊚ |
| 80/20 | ⊚ | ⊚ | ⊚ | ⊚ | ⊚ |
| 99.9/0.1 | ○ | ○ | ○ | ○ | ○ |
| 100/0 | X | Δ | Δ | Δ | ○ |

As shown in Table 3, at an A1/B1 ratio within the range from 55:45 to 99.9:0.1, especially within the range from 60:40 to 80:20, sedimentation or separation was not observed regardless of the solvent ratio, suggesting an extremely excellent stability over a prolonged period.

EXPERIMENT EXAMPLE 3

Effects of Cation Species

Using various cation-modified clay minerals, gel compositions were prepared similarly to Experiment Example 1 and examined for their thickening abilities. The results are shown in Table 4.

TABLE 4

| Cation-modified clay mineral | Ethyl acetate/n-butyl acetate ratio | | | | |
| --- | --- | --- | --- | --- | --- |
| | 0/100 | 25/75 | 50/50 | 75/25 | 100/0 |
| A1/A2 = 30/70 | X | X | Δ | Δ | Δ |
| A1/A3 = 50/50 | X | Δ | Δ | Δ | Δ |
| B1/B2 = 20/80 | Δ | Δ | Δ | X | X |

As shown in Table 4, any use of a combination of two Cation-modified clay minerals A or a combination of two Cation-modified clay minerals B was not successful in maintaining a high thickening ability over a wide range of the polarity. Accordingly, the advantageous property of the present invention is attributable specifically to a use of a combination of Cation-modified clay minerals A and B.

EXAMPLE 1
Nail Enamel

| | |
|---|---|
| Nitrocellulose | 20% by weight |
| Toluenesulfonamide resin | 15 |
| Acetyltributyl citrate | 5 |
| Camphor | 1 |
| Ethyl acetate + n-butyl acetate | 52.89 |
| Calcium stearate | 0.1 |
| Citric acid | 0.01 |
| n-Butanol | 1 |
| POE(1)POP(25)diethylmethylammonium chloride | 0.5 |
| Di-POE(2)myristyl ether phosphoric acid | 0.1 |
| Cation-modified clay minerals (A1 + B1) | 1.3 |
| Red#202 | 0.5 |
| Red#226 | 0.5 |
| Iron oxide red | 0.1 |
| Titanium oxide-coated mica | 1 |
| Iron oxide-coated mica | 1 |
| Total | 100 |

Using the formulation shown above, nail enamels were prepared at various ethyl acetate/n-butyl acetate ratio and various Cation-modified clay mineral A1/B1 ratio. As shown in Table 5, each nail enamel exhibited a satisfactory thickening ability and a satisfactory stability over a prolonged period over a wide range of the polarity.

TABLE 5

| | Ethyl acetate/n-butyl acetate ratio | | | |
|---|---|---|---|---|
| A1/B1 ratio | 19/81 | 38/62 | 76/24 | 95/5 |
| 58/42 (Thickening ability) | ○ | ○ | ○ | ○ |
| (Stability over a prolonged period) | ○ | ○ | ○ | ○ |
| 69/31 (Thickening ability) | ○ | ○ | ○ | ○ |
| (Stability over a prolonged period) | ○ | ○ | ○ | ○ |
| 77/23 (Thickening ability) | ○ | ○ | ○ | ○ |
| (Stability over a prolonged period) | ○ | ○ | ○ | ○ |

EXAMPLE 2
Nail Enamel

| | |
|---|---|
| Nitrocellulose | 15% by weight |
| Alkyd resin | 5 |
| Sugar ester resin | 5 |
| Acetyltriethyl citrate | 5 |
| Camphor | 3 |
| Ethyl acetate + n-butyl acetate | 60.68 |
| Calcium stearate | 0.1 |
| Citric acid | 0.02 |
| n-Butanol | 1 |
| POE(1)POP(25)diethylmethylammonium chloride | 0.5 |
| Di-POE(2)myristyl ether phosphoric acid | 0.1 |
| Cation-modified clay minerals (A1 + B1) | 1.5 |
| Red#202 | 0.5 |
| Red#226 | 0.5 |
| Iron oxide red | 0.1 |
| Titanium oxide-coated mica | 1 |
| Iron oxide-coated mica | 1 |
| Total | 100 |

Using the formulation shown above, nail enamels were prepared at various ethyl acetate/in-butyl acetate ratio and various Cation-modified clay mineral A1/B1 ratio. As shown in Table 6, each nail enamel exhibited a satisfactory thickening ability and a satisfactory stability over a prolonged period over a wide range of the polarity.

TABLE 6

| | Ethyl acetate/n-butyl acetate ratio | | | |
|---|---|---|---|---|
| A1/B1 ratio | 16/84 | 33/67 | 66/34 | 99/1 |
| 67/33(Thickening ability) | ○ | ○ | ○ | ○ |
| (Stability over a prolonged period) | ○ | ○ | ○ | ○ |
| 73/27(Thickening ability) | ○ | ○ | ○ | ○ |
| (Stability over a prolonged period) | ○ | ○ | ○ | ○ |
| 80/20(Thickening ability) | ○ | ○ | ○ | ○ |
| (Stability over a prolonged period) | ○ | ○ | ○ | ○ |

EXAMPLE 3
Nail Enamel

TABLE 7

| Component | 3-1 | 3-2 | 3-3 | 3-4 |
|---|---|---|---|---|
| Nitrocellulose | 20 | 20 | 20 | 20 |
| Toluenesulfonamide resin | 15 | 15 | 15 | 15 |
| Acetyltributyl citrate | 5 | 5 | 5 | 5 |
| Camphor | 1 | 1 | 1 | 1 |
| Ethyl acetate | 10 | 20 | 40 | 50 |
| n-Butyl acetate | to 100 | to 100 | to 100 | to 100 |
| Calcium stearate | 0.1 | 0.1 | 0.1 | 0.1 |
| Citric acid | 0.01 | 0.01 | 0.01 | 0.01 |
| n-Butanol | 1 | 1 | 1 | 1 |
| POE(1)POP(25)diethylmethyl ammonium chloride | 0.5 | 0.5 | 0.5 | 0.5 |
| Di-POE(2)myristyl ether phosphoric acid | 0.1 | 0.1 | 0.1 | 0.1 |
| Cation-modified clay mineral A4 | 0.9 | 0.9 | 0.9 | 0.9 |
| Cation-modified clay mineral B3 | 0.4 | 0.4 | 0.4 | 0.4 |
| Red#202 | 3.5 | 4.5 | 0.5 | 0.5 |
| Red#226 | 3.5 | 4.5 | 1.5 | 1.5 |
| Iron oxide red | 3.1 | 4.1 | 0.1 | 0.1 |
| Titanium oxide-coated mica | 1 | 1 | 1 | 1 |
| Iron oxide-coated mica | 1 | 1 | 1 | 1 |
| Thickening ability | ○ | ○ | ○ | ○ |
| Stability over a prolonged period | ○ | ○ | ○ | ○ |

EXAMPLE 4
Nail Enamel

TABLE 8

| Component | 4-1 | 4-2 | 4-3 | 4-4 |
|---|---|---|---|---|
| Nitrocellulose | 20 | 20 | 20 | 20 |
| Toluenesulfonamide resin | — | 15 | 15 | 15 |
| Alkyd resin | 7 | — | 10 | 10 |
| Sugar ester resin | — | — | 2 | 2 |
| Acryl resin | 7 | — | — | — |
| Acrylsilicone resin | — | 2 | — | 2 |
| Acetyltributyl citrate | 5 | 5 | 5 | 5 |
| Camphor | 1 | 1 | 1 | 1 |
| Ethyl acetate | 20 | 20 | 20 | 20 |
| n-Butyl acetate | to 100 | to 100 | to 100 | to 100 |
| Calcium stearate | 0.1 | 0.1 | 0.1 | 0.1 |
| Citric acid | 0.01 | 0.01 | 0.01 | 0.01 |
| n-Butanol | 1 | 1 | 1 | 1 |
| POE(1)POP(25)diethylmethyl ammonium chloride | 0.5 | 0.5 | 0.5 | 0.5 |
| Di-POE(2)myristyl ether phosphoric acid | 0.1 | 0.1 | 0.1 | 0.1 |
| Cation-modified clay mineral A1 | 0.9 | 0.9 | 0.9 | 0.9 |
| Cation-modified clay mineral B1 | 0.4 | 0.4 | 0.4 | 0.4 |
| Red#202 | 0.5 | 0.5 | 0.5 | 0.5 |
| Red#226 | 0.5 | 0.5 | 0.5 | 0.5 |
| Iron oxide red | 0.1 | 0.1 | 0.1 | 0.1 |
| Titanium oxide-coated mica | 1 | 1 | 1 | 1 |
| Iron oxide-coated mica | 1 | 1 | 1 | 1 |
| Thickening ability | ○ | ○ | ○ | ○ |
| Stability over a prolonged period | ○ | ○ | ○ | ○ |

EXAMPLE 5

Nail Enamel

| | |
|---|---|
| Ethyl acetate | 20.0 |
| n-Butyl acetate | to 100 |
| Acetyltributyl citrate | 5.0 |
| Sugar ester resin | 2.0 |
| Trimeritic acid-neopentylgrycol adipic acid-polyester resin (Uniplex 670P, manufactured by Unitex Chemical Corp.) | 10.0 |
| Nitrocellulose | 20.0 |
| Vitamin E acetate | 0.1 |
| Macadamia nut oil | 0.1 |
| Di-POE(2)myristyl ether phosphoric acid | 0.1 |
| Cation-modified clay mineral B1 | 0.4 |
| Cation-modified clay mineral A1 | 0.8 |
| POE(1)POP(25)diethylmethylammonium chloride | 0.4 |
| n-Butanol | 0.5 |
| Calcium stearate | 0.1 |
| Octylmethoxy cinnamate | 0.2 |
| Coloring material | 2.0 |
| Pearl luster material | 1.0 |
| Pearly pigment | 1.0 |

Each evaluation with respect to the nail enamel of Example 5 was ⊚ in both of a thickening ability and stability over a prolonged period.

As described above, a use of certain two cations as cations of cation-modified clay mineral enables a production of a gel composition capable of maintaining a high viscosity controlling ability over a wide polarity range from a low polarity to a high polarity and also capable of exhibiting an excellent viscosity stability over a prolonged period as well as such nail enamel.

We claim:

1. A gel composition comprising a cation-modified clay mineral, wherein cations of said cation-modified clay mineral comprise quaternary ammonium cations represented by Formula (I):

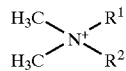

(I)

wherein $R^1$ is a $C_{1-9}$ alkyl group, a phenyl group, or a $C_{7-9}$ aralkyl group, that is an aryl ring with a 1 to 3 carbon substitutent, and $R^2$ is a $C_{10-36}$ alkyl group;

and formula (II):

(II)

wherein $R^3$ and $R^4$ are independent from each other and each represents a $C_{10-36}$ alkyl group; and wherein said cation-modified clay mineral comprises the cation-modified clay mineral A whose cation is the quaternary ammonium cation represented by the Formula (I) and the cation-modified clay mineral B whose cation is the quaternary ammonium cation represented by the Formula (II) in a weight ratio of A:B from 55:45 to 99.9:0.1.

2. The gel composition according to claim 1, wherein the weight ratio of A:B is from 60:40 to 80:20.

3. The gel composition according to claim 1, wherein $R^1$ is benzyl group.

4. The gel composition according to claim 1, wherein $R^1$ is methyl group.

5. The gel composition according to claim 1, wherein $R^2$ is a $C_{16-18}$ alkyl group.

6. The gel composition according to claim 1, wherein each of $R^3$ and $R^4$ is a $C_{16-18}$ alkyl group.

7. The gel composition according to claim 1, wherein a host clay mineral of said cation-modified clay mineral is montmorillonite or hectorite.

8. The gel composition according to claim 7, wherein the host clay mineral of said cation-modified clay mineral is montmorillonite.

9. A nail enamel comprising the gel composition according to claim 1.

* * * * *